(12) United States Patent
Ferenz et al.

(10) Patent No.: US 7,825,207 B2
(45) Date of Patent: Nov. 2, 2010

(54) SILOXANES CONTAINING GUANIDINO GROUPS AND USE THEREOF FOR COSMETIC FORMULATIONS

(75) Inventors: Michael Ferenz, Essen (DE); Holger Leidreiter, Hattingen (DE); Matthias Pascaly, Muenster (DE)

(73) Assignee: Goldschmidt GmbH (DE)

( * ) Notice: Subject to any disclaimer, the term of this patent is extended or adjusted under 35 U.S.C. 154(b) by 1266 days.

(21) Appl. No.: 11/343,054

(22) Filed: Jan. 30, 2006

(65) Prior Publication Data

US 2006/0188455 A1    Aug. 24, 2006

(30) Foreign Application Priority Data

Feb. 2, 2005    (DE)    ........................ 10 2005 004 704

(51) Int. Cl.
*C08G 77/26*    (2006.01)
(52) U.S. Cl. ............................. 528/28; 528/38; 528/34; 556/424; 424/70.122
(58) Field of Classification Search .................. 556/424; 424/70.122; 528/28, 38, 34
See application file for complete search history.

(56) References Cited

U.S. PATENT DOCUMENTS 3,725,502 A * 4/1973 Bernheim et al. ........... 528/111

FOREIGN PATENT DOCUMENTS

| DE | 506 282 | 9/1930 |
| DE | 101 14 561 A1 | 9/2002 |
| DE | 101 19 608 A1 | 10/2002 |
| DE | 103 27 871 A1 | 1/2005 |
| EP | 1 493 423 A1 | 1/2005 |
| JP | 6263621 | 9/1994 |
| JP | 1017442 | 1/1998 |
| JP | 1135424 | 2/1999 |
| JP | 2002-167437 | 6/2002 |

\* cited by examiner

*Primary Examiner*—Margaret G Moore
(74) *Attorney, Agent, or Firm*—Frommer Lawrence & Haug LLP

(57) ABSTRACT

The invention relates to polysiloxanes containing guanidino groups for which the guanidino groups can be combined arbitrarily with other functional groups on the polysiloxane backbone according to the general formula (I)

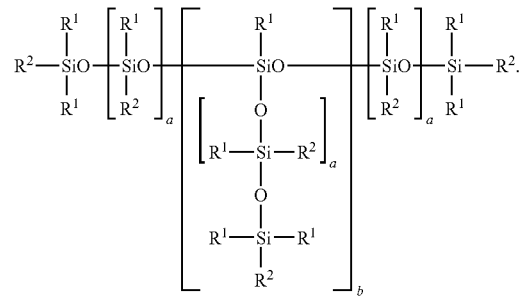

13 Claims, No Drawings

SILOXANES CONTAINING GUANIDINO GROUPS AND USE THEREOF FOR COSMETIC FORMULATIONS

Any foregoing applications, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

Citation or identification of any document in this application is not an admission that such document is available as prior art to the present invention.

Terms "comprising" and "comprises" in this disclosure can mean "including" and "includes" or can have the meaning commonly given to the term "comprising" or "comprises" in US Patent Law. Terms "consisting essentially of" or "consists essentially of" if used in the claims have the meaning ascribed to them in US Patent Law. Other aspects of the invention are described in or are obvious from (and within the ambit of the invention) the following disclosure.

Human hair is subjected daily to a wide variety of influences. Besides mechanical stresses as a result of brushing, combing, wearing the hair up or tying it back, the hair is also attacked by environmental influences, such as, for example, strong UV radiation, cold, wind and water. The physiological status (e.g. age, health) of the particular person also influences the damage to the keratin fibers.

The treatment with chemical compositions also changes the structure and surface properties of the hair. Methods such as, for example, permanent waving, bleaching, coloring, tinting, smoothing etc., but also frequent washing with aggressive surfactants contribute to causing greater or lesser damage to the structure of the hair. Thus, for example, during a permanent wave, both the cortex and also the cuticula of the hair are attacked. The disulfide bridges of the cystine are broken as a result of the reducing step and oxidized in part to give cysteic acid in the subsequent oxidizing step.

During bleaching, not only is the melanin destroyed, but in addition about 15 to 25% by weight of the disulfide bonds of the cystine are oxidized during mild bleaching. During excessive bleaching, it can even be up to 45% by weight (K. F. de Polo, A Short Textbook of Cosmetology, 2000, Verlag für chemische Industrie, H. Ziolkowsky GmbH).

Thus, the chemical treatments, the frequent washing or the UV irradiation result in disadvantageous mechanical properties for the hair, caused by the removal of naturally secreted hair grease or humectants (sebum). As a result, it becomes brittle, dry, dull, porous and difficult to comb. Furthermore, thoroughly cleansed hair is usually very difficult to comb, both in the wet state and also in the dry state since the individual hairs have a tendency to go fizzy and become tangled. It thus loses its strength firstly during washing and then during combing. This is apparent from a significant decrease in the stress-strain forces and the tear forces for wet hair. In addition, it is less resistant to further damage by chemicals, surfactants and environmental influences than healthy hair.

There are special preparations for repairing hair damaged in this way, such as, for example, hair rinses, hair treatments, shampoos, leave-in conditioners, etc., although these are primarily able to improve the combability, the feel and the shine of damaged hair. Such standard commercial haircare compositions comprise primarily cationic surfactants based on alkylammonium, polymers, waxes and oils or silicone oils. The effectiveness of these compounds can be attributed to an electrostatic interaction of the cationic quat groups or rather to a hydrophobization of the surface of the hair. However, (bio) chemical repair of the hair is not achieved as a result.

The problem of loss/reduction of mechanical strength in the hair as a result of damage has long been a problem in the art.

One attempt to solve this problem is the use of creatine. DE-A-101 14 561 and DE-A-101 19 608 refer to the use of creatine compounds in compositions for hardening, strengthening, restructuring or increasing the shine, volume or combability of keratin fibers, in particular human hair.

A disadvantage of using creatine is the fact that creatine can only be formulated via the aqueous phase and it is always in an equilibrium with creatine in aqueous solutions and thus is no longer available as active substance for the hair. Furthermore, being a monomeric compound of low molecular weight, it is easily washed out of the fabric or surface to be treated (skin or hair) again.

The use of creatine-like compounds for use in hair treatment compositions and hair aftertreatment compositions for repair and conditioning is also described in the unpublished literature DE-103 27 871.0 and EP-03013799.6. These and numerous other specifications (DE-506 282, JP-A-6-263621, JP-11035424, JP-10017442) describe the extremely diverse methods for producing a very wide variety of alkyl guanidines. Only JP-2002167437 describes, starting from amodimethicones, the production and use of simple linear silicone-containing guanidines. These are used for hair treatment with hair cosmetics and for fiber treatment compositions.

Other effects and uses of guanidinium-containing silicone compounds are hitherto not known in the literature. Combinations of different functional groups in silicones beside guanidino groups are also not disclosed. Furthermore, the production of guanidinium-containing silicone monomers and their subsequent polymerization is unknown.

Against this background, there is a need in the art to identify further novel substances which achieve a similar physiological effect or else aid and enhance the effect of creatine, have a polymeric structure and, in addition to the advantageous properties of the polysiloxanes, have effects which condition, protect and repair the hair. In this context, further functional groups beside guanidino groups can also be inserted into the silicone.

There is also a need for active ingredients which can be widely used for hair treatment compositions and hair aftertreatment compositions which improve the mechanical strength of the hair, protect the hair against further damage to the hair structure and minimize the existing structural damage to the hair caused by environmental influences and shaping and coloring treatments, and which can be produced in a simple way and allow various functional groups to be combined independently of one another.

It is an object of the invention to provide such an active ingredient which is able both to improve the mechanical strength of damaged hair and also to protect the hair against damage by chemical treatment or exogenous factors. The compounds should thus exhibit a combined effect. Firstly, they should act as conditioners and improve the shine, the combability, the softness, the volume, the shapeability, the handleability and the detangleability (ability to untangle or prevent the tangling) of the hair and at the same time the compounds according to the invention should protect the hair against damage and make it more resistant and/or repair said damage. In this connection, it should be possible to adjust the properties of the compounds in a targeted manner by freely combining the substituents on the silicone backbone.

The invention therefore provides polysiloxanes containing guanidino groups and of the general formula (I)

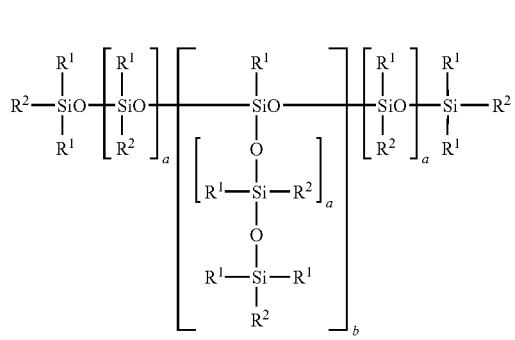
(I)

in which the radicals $R^1$ are identical or different and are an optionally branched hydrocarbon radical which optionally contains double bonds and has 1 to 30 carbon atoms, preferably 1 to 4 carbon atoms, or phenyl radicals or —$OR^{11}$ or —OH, $R^2$ independently of one another is $R^1$ or are radicals of the formulae (Ia, Ib or Ic)

$R^2$=-M-G  (Ia)

$R^2$=-M-$Q^+A^-$  (Ib)

$R^2$=-(M)$_x$-S  (Ic)

with the proviso that, in the average molecule, at least one radical $R^2$ is a radical of the formula -M-G (Ia), in which G is a guanidino group with the general formula (Ia$^1$, Ia$^2$)

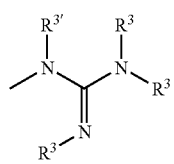
(Ia$^1$)

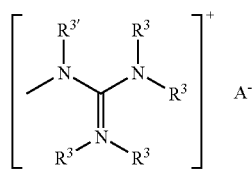
(Ia$^2$)

and/or salts or hydrates thereof, in which $R^3$ independently of the others, is hydrogen or an optionally branched hydrocarbon radical optionally comprising double bonds, or $R^{3'}$ may be $R^3$ or an alkylene group which is joined to M via carbon atoms or heteroatoms and forms a 5- to 8-membered ring, and M is a divalent or polyvalent hydrocarbon radical having at least 3 carbon atoms which has one hydroxyl group and which can be interrupted by one or more oxygen atoms or nitrogen atoms or quaternary ammonium groups or ester or amide functions, $Q^+$ is a radical of the formula (Id)

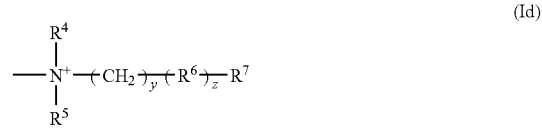
(Id)

$R^4$, $R^5$ are alkyl radicals having 1 to 4 carbon atoms, $R^6$ is

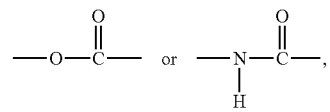

$R^7$ may be a monovalent hydrocarbon radical having 1 to 22 carbon atoms, y is 0 to 6 z is 0 or 1, $A^-$ is an inorganic or organic anion which originates from a customary physiologically compatible acid HA, S is H, a polyalkylene oxide polyether of the general formula $C_mH_{2m}O(C_2H_4O)_n(C_3H_6O)_oR^8$ in which m is 1 to 6, in particular 3 to 6, n,o independently of one another are 0 to 100, in particular 0 to 20 and the polyether has a molecular weight between 100 and 6000 g/mol and $R^8$ is H or an optionally branched aromatic or alicyclic hydrocarbon radical optionally containing double bonds and having 2 to 30 carbon atoms, preferably 4 to 22 carbon atoms, or a UV-absorbing group, in particular cinnamic acid or methoxycinnamic acid, x is 0 or 1 and a independently of the others has a value of from 4 to 1000, preferably 20 to 200, and b has a value from 0 to 10

$R^{11}$ is an aliphatic or aromatic hydrocarbon radicals having 1 to 30, preferably 1 to 4, carbon atoms which are optionally branched or H.

In one embodiment of the invention, $R^1$ is selected from the group consisting of be a methyl, ethyl, n-propyl, isopropyl, n-butyl, iso-butyl and phenyl radical.

In one embodiment of the invention, the number of carbon atoms for the hydrocarbon defined in $R^3$ is from 1-20 carbon atoms, preferably 1-8 carbon atoms and more preferably 1-4 carbon atoms. It is understood by those of skill in the art that the lower ranges would be 2 when at least one double bond is present.

In one embodiment of the invention, the number of carbon atoms for the hydrocarbon defined in $R^{3'}$ is from 1-6 carbon atoms, preferably 2-4 carbon atoms and more preferably 3-5 carbon atoms. The number of heteroatoms is from 0-2, and is selected from the group consisting of N, O or S. A preferred heteroatom is N or O, more preferably N. In another embodiment of this invention, the size of the heterocyclic ring is a 5-6 membered ring.

In one embodiment of the invention, the number of carbon atoms in the hydrocarbon radical is from 4-20 carbon atoms, preferably 4-12, most preferably 4-6 carbon atoms.

In one embodiment of the invention, $R^4$ and $R^5$ are methyl.

In one embodiment of the invention, $R^7$ has 1-8 carbon atoms, preferably 1-4 carbon atoms.

In one embodiment of the invention, M is selected from the group consisting of:

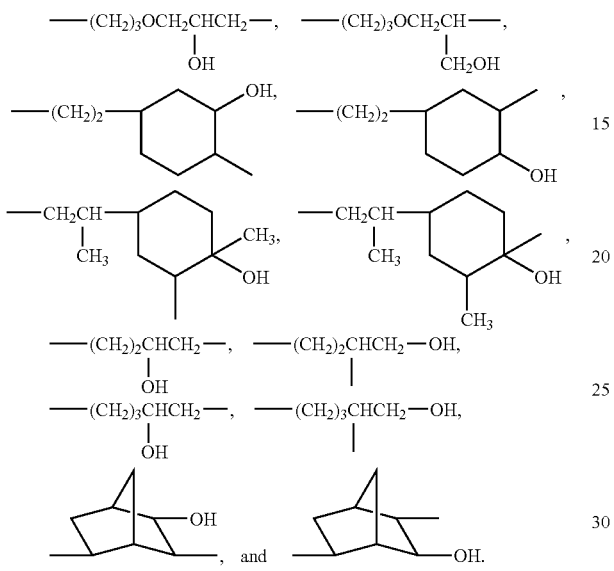

In one embodiment of the invention, each Q is identical or different and is a cationic radical selected from the group consisting of capryldimethylamine, lauryldimethylamine, cocodimethylamine, myristyldimethylamine, cetyldimethylamine, stearyldimethylamine, behenyldimethylamine, oleyldimethylamine, capryloylamidopropyldimethylamine, lauramidopropyldimethylamine, cocamidopropyldimethylamine, myristamidopropyldimethylamine, palmitamidopropyldimethylamine, stearamidopropyldimethylamine, behenamidopropyldimethylamine, oleamidopropyldimethylamine, undecylenamidopropyldimethylamine, ricinoleamidopropyldimethylamine, and guanidinopropyldimethylamine.

In one embodiment of the invention, $A^-$ includes but is not limited to, an inorganic or organic anion, which originate from a customary physiologically compatible acid HA, such as formic acid, acetic acid, propionic acid, heptanoic acid, caprylic acid, nonanoic acid, capric acid, undecanoic acid, lauric acid, myristic acid, palmitic acid, stearic acid, arachidic acid, behenic acid, cyclopentanecarboxylic acid, cyclohexanecarboxylic acid, acrylic acid, methacrylic acid, vinylacetic acid, crotonic acid, 2-/3-/4-pentenoic acid, 2-/3-/4-/5-hexenoic acid, lauroleic myristoleic acid, palmitoleic acid, oleic acid, gadoleic acid, sorbic acid, linoleic acid, linolenic acid, pivalic acid, ethoxyacetic acid, phenylacetic acid, lactic acid, 2-ethylhexanoic acid, oxalic acid, glycolic acid, malic acid, malonic acid, succinic acid, tartaric acid, glutaric acid, citric acid, adipic acid, pimelic acid, suberic acid, azelaic acid, sebacic acid, benzoic acid, o-/m-/p-toluic acid, phenylacetic acid, salicylic acid, 3-/4-hydroxybenzoic acid, phthalic acids or completely or partially hydrogenated derivatives thereof, such hexahydro- or tetrahydrophthalic acid, carbonic acid, phosphoric acid, hydrochloric acid, sulfuric acid and mixtures thereof, in particular lactic acid, tartaric acid, acetic acid and hydrochloric acid. In this connection, for the purposes of the present invention, it is also possible to use either suitable silicone guanidine derivatives in mixtures with one another, or else mixed salts.

This invention further provides silicone guanidine derivatives which are obtained by reacting silanes containing guanidino groups and of the general formula II with one or more different silanes of the general formula III and one or more different OH- or $OR^{11}$-functional siloxanes of the general formula IV, optionally in the presence of a catalyst which promotes condensation and/or water and emulsifiers

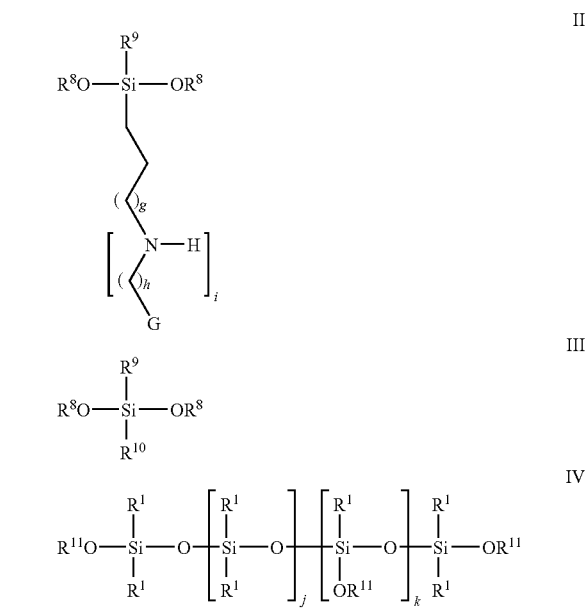

in which
$R^8$ are identical or different and are hydrocarbon radicals having 1 to 30 carbon atoms, preferably hydrocarbon radicals having 1 to 2 carbon atoms or phenyl radicals, $R^9$ are identical or different and are hydrocarbon radicals having 1 to 30 carbon atoms, preferably hydrocarbon radicals having 1 to 2 carbon atoms or phenyl radicals, or $OR^8$ radicals, g is 0 to 10, preferably 1 to 3, h is 1 to 11, preferably 1 to 4, i is 0 to 3, preferably <2, $R^{10}$ are aliphatic or aromatic hydrocarbon radicals having 1 to 30 carbon atoms, preferably hydrocarbon radicals having 1-18 carbon atoms, more preferably hydrocarbon radicals having 1-10 carbon atoms, which are optionally branched and carry one or more amine or OH or SH groups and are optionally interrupted by amine or ether functions, or $OR^8$ or polyethers, preferably ethers or polyethers, $R^{11}$ are aliphatic or aromatic hydrocarbon radicals having 1 to 30, preferably 1 to 4, carbon atoms which are optionally branched or H, k is between 0 and 10, preferably 0 to 5, and j is between 8 and 1000.

The invention further provides a method of producing these compounds wherein a siloxane containing at least one epoxy group is reacted at elevated temperature with guanidine compounds of the general formula

Z-G, in which
G has the meaning given above and

Z is a hydrocarbon radical containing at least 2 carbon atoms, preferably 3 to 6, and optionally comprising heteroatoms such as N, O or S, in particular N, which may be bonded to $R^{3'}$ via a carbon atom or heteroatom and in so doing forms a 5- to 8-membered ring, and/or salts thereof by methods known per se.

The invention further provides a method of producing these compounds wherein silanes containing guanidino groups and of the general formula II are mixed with one or more different silanes of the general formula III and one or more different OH- or $OR^{11}$-functional siloxanes of the general formula IV, in the presence of a catalyst which promotes condensation, and are heated, optionally in the presence of water and one or more emulsifiers.

The person skilled in the art is aware that the compounds are present in the form of a mixture with a distribution which is essentially controlled by the laws of statistics. The values of the indices a and b therefore represent average values.

The invention further provides the use of the compounds according to the invention as conditioners for producing cosmetic formulations for hair treatment and hair aftertreatment which at the same time bring about an improvement in the structure or mechanical strength of the hair.

The silicone guanidines used or co-used according to the invention have both good stability and also good formulatability, bring about a considerable effect even at low use concentrations and are not toxic, are very well tolerated by the hair and the scalp, have high compatibility with other ingredients and can be incorporated into hair treatment compositions without problems. In addition, they may also have a antimicrobial effect.

The compounds according to the invention thus combine different functional groups on the silicone backbone. These very combinations give rise not only to the conditioning effect for the hair, but also to an improvement in the fiber strength (elongation strength and modulus of elasticity are increased). This effect is generally also referred to as the repair effect. As a result of the high affinity of the guanidine group to the keratin of the hair, a lasting effectiveness is observed. The properties of the compounds can be adjusted in a targeted manner independently of one another and be matched to one another in accordance with the building block principle.

In care formulations for porous surfaces such as leather, wood or furniture, a very good increase in shine on the treated surfaces is obtained with silicone guanidines. As a result of their substantivity, they give a long-lasting protective film which prevents resoiling as a result of its antistatic effect. As a result of their hydrophobic properties, they additionally prevent rapid through-wetting of porous materials. Care formulations in the form of emulsions usually comprise 1 to 3% emulsifiers, 3 to 5% waxes, 2 to 5% oils and 0.5 to 1% thickeners in aqueous solution by weight based on the total weight of the formulation. Emulsifiers, waxes, oils and thickeners include but are not limited to those known in the art, e.g. as described in *The International Cosmetic Ingredient Dictionary and Handbook*, $9^{th}$ Edition (2002). For this, 0 to 5% and in particular 1 to 3% of the silicone guanidine compound according to the invention are used in order to significantly increase the abovementioned properties.

In care formulations for smooth surfaces, such as metallic or painted surfaces, a very good increase in shine on the treated surfaces is obtained with silicone guanidines without attaining excessive greasiness of the surfaces. As a result of their substantivity, they give a long-lasting protective film which prevents resoiling as a result of its antistatic effect. The use of the silicone guanidine reduces the customary care substances and thus the impressions referred to as fingerprints, which arise when using care substances such as oils or waxes, are also reduced. Care emulsions for smooth surfaces usually comprise 0 to 10% emulsifiers, 1 to 8% waxes, 2 to 8% oils, in most cases silicone oils, and 0.5 to 1% thickeners in aqueous solution by weight based on the total weight of the formulation. For this 0 to 5% and particularly 1 to 3% of the silicone guanidine compound according to the invention are used in order to significantly increase the abovementioned properties.

In drying auxiliaries for car washes, the silicone guanidine compounds according to the invention are added to the microemulsions customary for this purpose in order, here too, to generate a long-lasting protective film as a result of their substantivity. This prevents resoiling as a result of its antistatic effect and thus produces a long-lasting shine. Customary drying auxiliaries comprise 0.1 to 5% by weight of the silicone guanidine compound according to the invention in order to produce this effect. The drying auxiliary described is a cationic microemulsion formulated from one or more quaternary compounds, use amount generally 5 to 25% by weight and one or more hydrophobic oils, use amount generally 3 to 30% by weight, which are optionally stabilized with coemulsifiers, use amount generally 0 to 5% by weight.

Preferred examples of polysiloxanes containing guanidinium groups are compounds of the general formula (I)

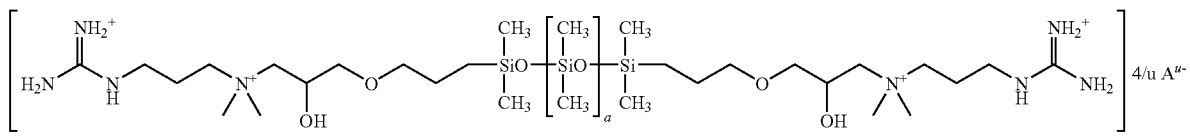

$a=8, 28, 48, 78$; $u=$valence of the anion

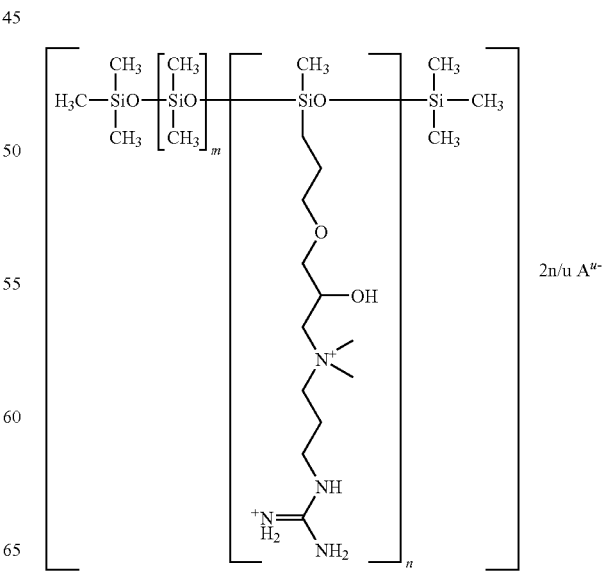

m=83, 73, 13; n=5, 25

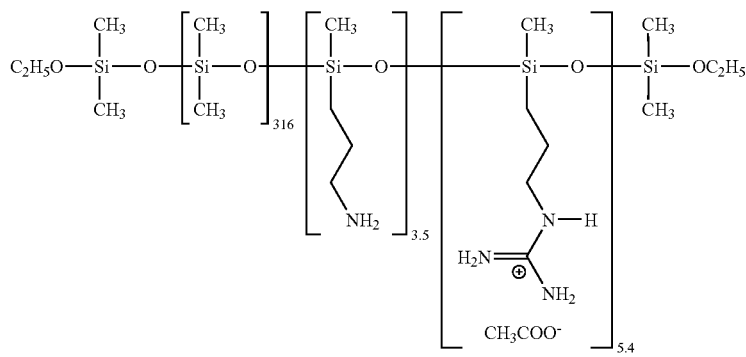

The invention is further described by the following non-limiting examples which further illustrate the invention, and are not intended, nor should they be interpreted to, limit the scope of the invention.

EXAMPLES

Methods for producing the compounds according to the invention and the properties of these compounds are described in more detail in the examples below:

A precursor (1-(3-N,N-aminopropyl)guanidinium acetate) for producing quaternary silicone guanidines was synthesized in accordance with a procedure described in DE-506 282 or DE-103 27 871.0 and EP-03013799.6.

Example 1

Preparation of a guanidino polysiloxane according to the invention of the general formula:

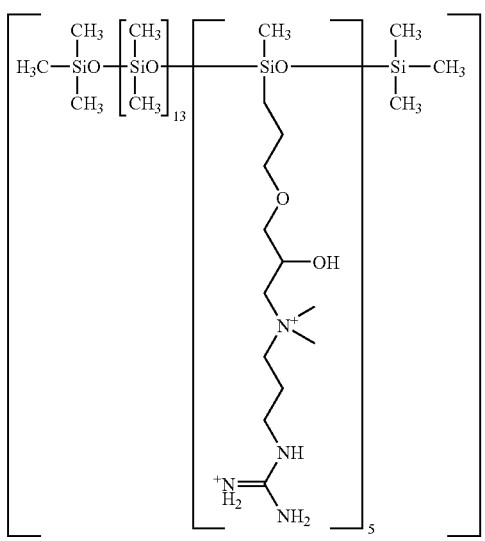

10 g (0.1 mol) of a tertiary amine containing guanidinium group (present as acetate) and of the formula

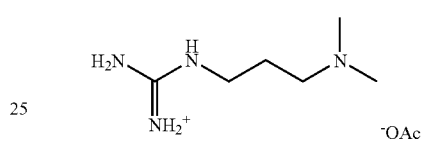

are initially introduced together with 3 g (0.103 mol) of acetic acid and 40 ml of isopropanol into a 250 ml four-necked flask fitted with stirrer, dropping funnel, thermometer and reflux condenser. After about 1 hour, 19.5 g (0.1 mol of epoxy) of an epoxy siloxane (these are prepared by a known method by hydrosilylation with allyl glycidyl ether) of the formula

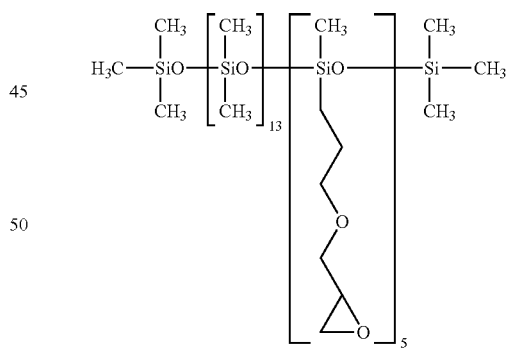

are added dropwise, heated to reflux temperature and stirred for 6 hours. The mixture is then distilled at 80° C. under reduced pressure. A high-viscosity yellow product is obtained.

Example 2

Preparation of a guanidino polysiloxane according to the invention and of the general formula:

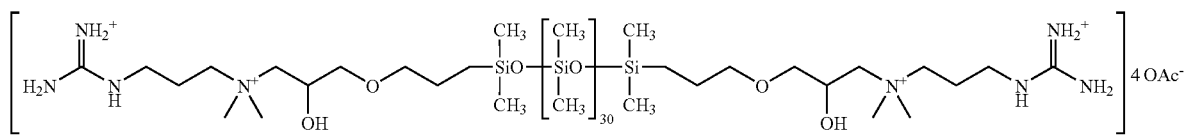

20.4 g (0.1 mol) of the tertiary amine mentioned in example 1 are initially introduced together with 6.2 g (0.1 mol) of acetic acid in 40 ml of isopropanol into a 250 ml four-necked flask fitted with stirrer, dropping funnel, thermometer and reflux condenser. After 1 hour at the reflux temperature, 113 g (0.1 mol of epoxy) of an epoxy siloxane of the general formula

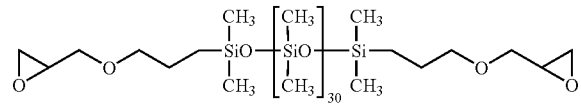

are added dropwise, heated to the reflux temperature and stirred for 6 hours. The mixture is then distilled at 100° C. under reduced pressure. A wax-like, yellow product is obtained.

Example 3

Preparation of a guanidino polysiloxane according to the invention of the general formula:

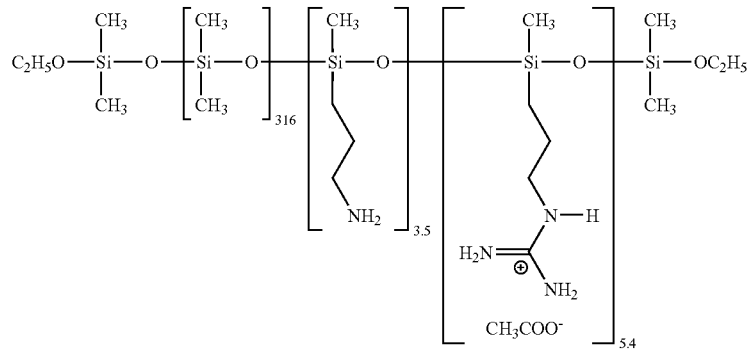

70 g of water, 40 g of fatty alcohol ethoxylate, 10 g of 50% strength aqueous sodium hydroxide solution, 10 g of a guanidino-group-containing silane $MeSi(OEt)_2\text{-}(CH_2)_3\text{—}NHC(NH_2)\text{=}NH_2^+CH_3COO^-$, 10 g of an aminofunctional siloxane $MeSi(OEt)_2\text{-}(CH_2)\text{—}NH_2$ and 240 g of a silanol of the formula $HO\text{—}SiMe_2O\text{—}(SiMe_2O)\text{—}SiMe_2OH$ are stirred together in a 250 ml flask. The mixture is heated to 70° C. and left to react for 4 hours. It is then diluted with 130 ml of water and neutralized with acetic acid. This gives an aqueous emulsion of the abovementioned guanidino-group-containing siloxane.

Example 4

To test the effects of the compounds of the invention in hair treatment, the following guanidino polysiloxanes according to the invention (present with acetate as counterion) were used:

Compounds 1 and 2 according to structural formula:

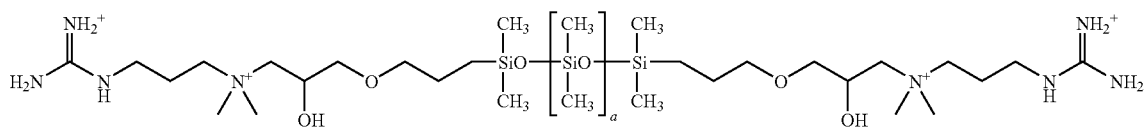

where compound 1 has a=8 and compound 2 has a=28.

Compounds 3 and 4 according to structural formula:

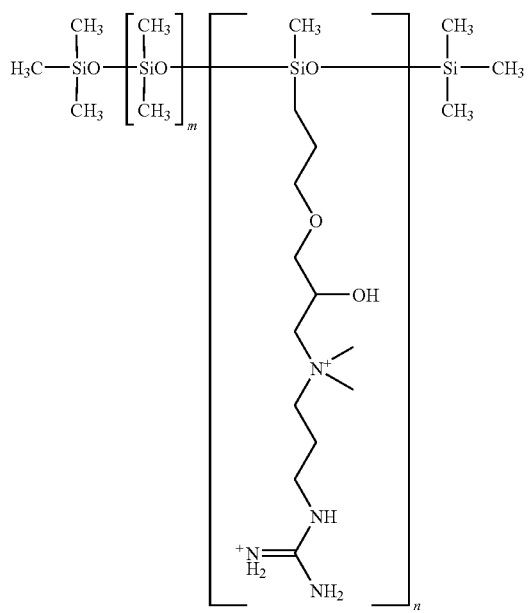

where compound 3 has m=13 and n=5 and compound 4 has m=83 and n=5.

Preparation and investigation of hair treatment compositions using the compounds 1, 2 and 3 according to the invention:

For the applications-related assessment, hair tresses which are used for sensory tests are predamaged in a standardized way by a permanent wave treatment and a bleaching treatment. For this, products which are customary for styling are used.

Materials:
Permanent wave liquid (e.g. "ondi", Wella)
Neutralizer (e.g. "neutrafix", Wella)
Bleaching powder (e.g. "blondor special", Wella)
$H_2O_2$ (e.g. "Welloxyd 9%", Wella)
Shampoo without care component (e.g. sodium lauryl ether sulfate (12% WAS), NaCl thickened)
Beakers
Hair coloring brush The treatment is carried out in the following order:
1. Permanent wave treatment:
The hair tresses are wetted with the permanent wave liquid (weight ratio of hair:liquid=1:2). After a contact time of 15 min at room temperature in a covered beaker, the permanent wave liquid is carefully rinsed out for 2 min. The hair tresses are then gently squeezed using a towel. The neutralization (ratio of hair:liquid=1:2) has a contact time of 10 min at room temperature. The neutralizer is then carefully rinsed out for 2 min. The hair is then dried overnight at room temperature.
2. Bleaching treatment:
The bleaching powder and the $H_2O_2$ are processed to give a paste (weight ratio of powder:$H_2O_2$=2:3). The paste is then immediately applied to the permanently waved hair using a brush. The contact time is 30 min at room temperature. The bleaching paste is then rinsed out under running water for 2 min.
The hair is then washed with a shampoo without conditioner for 1 min (amount of shampoo: 0.5 ml/hair tress) and then rinsed out for 1 min.

Before the predamaged hair tresses are used for sensory tests, they are dried overnight at room temperature.

Test Formulation:
The conditioning products are tested in a simple hair rinse with the following composition

| Product | Weight fractions |
|---|---|
| TEGINACID ® C | 0.5% |
| Ceteareth-25 | |
| TEGO ® alkanol 16 | 2.0% |
| Cetyl alcohol | |
| Conditioner | 2.0% |
| Water | ad 100% |
| Citric acid | ad pH 4.0 ± 0.3 |

"Conditioner" refers to the compound examples according to the invention or comparison products.

Standardized treatment of predamaged hair tresses with conditioning samples:

The hair tresses predamaged as described above are treated as follows with the above-described conditioning rinse:

The hair tresses are wetted under running warm water. The excess water is gently squeezed out by hand, then the rinse is applied and gently worked into the hair (1 ml/hair tress (2 g)). After a residence time of 1 min, the hair is rinsed for 1 min.

Prior to the sensory assessment, the hair is dried in the air at 50% atmospheric humidity and 25° C. for at least 12 h.

Assessment Criteria:
The sensory evaluations are made according to grades which are awarded on a scale from 1 to 5, with 1 being the poorest evaluation and 5 being the best evaluation.

Wet Combability:

| Evaluation | Toothing of the comb | Result |
|---|---|---|
| 5 | coarse | No knots, the hair can be detangled easily |
| | fine | Very easy to comb through, no resistance detectable |
| 4 | coarse | Individual knots, the hair can be detangled easily |
| | fine | Easy to comb through, slight resistance detectable |
| 3 | coarse | A few knots, slight resistance |
| | fine | Some degree of resistance detectable, which decreases after repeated combing |
| 2 | coarse | Some knots, notable resistance |
| | fine | Notable resistance which does not decrease after repeated combing |
| 1 | coarse | Many knots, severe resistance |
| | fine | Very severe resistance, sometimes the hair cannot be combed through |

Wet Feel:

| Evaluation | Result |
|---|---|
| 5 | Very smooth, soft but nevertheless beautifully strong, of good feel, not greasy/tacky (no residues detectable) |
| 4 | Smooth and soft and/or only minimal residues detectable |
| 3 | Smooth, somewhat hard and/or some residues detectable |
| 2 | Hard and/or notably greasy, waxy residues |
| 1 | Very hard, rough, harsh and/or extremely greasy, tacky (clearly detectable greasy, waxy residues detectable) |

Dry Combability:

| Evaluation | Toothing of the comb | Result |
|---|---|---|
| 5 | coarse | No knots, the hair can be detangled easily |
|   | fine | Very easy to comb through, no resistance detectable, the hair does not become charged |
| 4 | coarse | Individual knots, the hair can be detangled easily |
|   | fine | Easy to comb through, slight resistance detectable, the hair becomes charged to a minimal degree |
| 3 | coarse | A few knots, slight resistance |
|   | fine | Some resistance detectable which decreases after repeated combing, the hair becomes slightly charged |
| 2 | coarse | Some knots, notable resistance |
|   | fine | Notable resistance which does not decrease after repeated combing, the hair becomes charged |
| 1 | coarse | Many knots, severe resistance |
|   | fine | Very severe resistance, sometimes the hair cannot be combed through, the hair becomes considerably charged |

Dry Feel:

| Evaluation | Result |
|---|---|
| 5 | Very smooth, soft but nevertheless strong, full, of good feel |
| 4 | Smooth and soft |
| 3 | Smooth, slightly hard and/or slightly harsh (residues) |
| 2 | Hard, somewhat harsh |
| 1 | Rough, hard, dry, harsh (residues) |

Dry Appearance:

| Evaluation | Result |
|---|---|
| 5 | Extremely shiny |
| 4 | Shiny |
| 3 | Somewhat shiny |
| 2 | Slightly shiny, slightly harsh |
| 1 | Harsh, no shine |

Table 1 below compares the results of the sensory assessment of the treatment of the hair tresses with substances according to the invention or comparative example is carried out as described above.

TABLE 1

| | Formulation "simple hair rinse" with | | | | |
|---|---|---|---|---|---|
| | Wet combability | Wet feel | Dry combability | Dry feel | Shine |
| Compound 1 | 4.5 | 4.25 | 3.75 | 4.0 | 3.75 |
| Compound 2 | 5.0 | 4.75 | 3.5 | 4.25 | 4.25 |
| Compound 3 | 4.5 | 4.25 | 3.5 | 4.25 | 4.0 |
| Compound 4 | 4.0 | 4.5 | 4.0 | 4.75 | 4.5 |
| Comparison compound cetrimonium chloride | 4.75 | 4.5 | 4.25 | 3.75 | 3.0 |
| Control without conditioner | 1.5 | 1.5 | 2.25 | 2.75 | 3.5 |

It is clear that the compound examples according to the invention receive very good cosmetic evaluations in the sensory assessment. Surprisingly, the compounds of the invention show similar or better cosmetic evaluation than other known conditioners (e.g. cetrimonium chloride) with unexpected improvements in dry feel and shine while maintaining the performance characteristics with respect to wet combability, wet feel and dry combability.

Having thus described in detail preferred embodiments of the invention, it is to be understood that the invention defined by the appended claims is not to be limited to particular details set forth in the above description as many apparent variations thereof are possible without departing from the spirit or scope of the invention. Thus, it is intended that the present invention covers the modifications and variations of this invention that come within the scope of any claims and their equivalents.

The invention claimed is:

1. A polysiloxane containing guanidino groups and of the general formula (I)

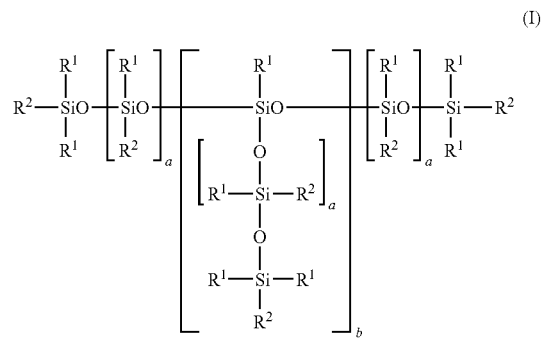

in which the radicals $R^1$ are identical or different and are an optionally branched hydrocarbon radical which optionally contains double bonds and has 1 to 30 carbon atoms or phenyl radicals or —$OR^{11}$ or

—OH, $R^2$ can in part have the meaning of the radicals $R^1$ and the other radicals $R^2$, independently of one another, are radicals of the formulae (Ia, Ib or Ic)

with the proviso that, in the average molecule, at least one radical $R^2$ is a radical of the formula -M-G (Ia), in which G is a guanidino group with the general formula ($Ia^1$, $Ia^2$)

-continued

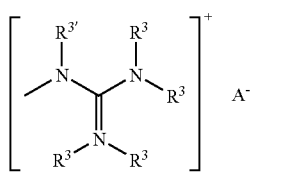
(Ia²)

and/or salts or hydrates thereof, in which
R³ a) independently of the others, is hydrogen or an optionally branched hydrocarbon radical optionally comprising double bonds,
R³' is R³ or an alkylene group which is joined to M via carbon atoms or heteroatoms and in so doing forms a 5- to 8-membered ring, and
M is a divalent or polyvalent hydrocarbon radical having at least 4 carbon atoms which has one hydroxyl group and which can be interrupted by one or more oxygen atoms or nitrogen atoms or quaternary ammonium groups or ester or amide functions,
$Q^+$ is a radical of the formula (Id)
$R^4$, $R^5$ are alkyl radicals having 1 to 4 carbon atoms,

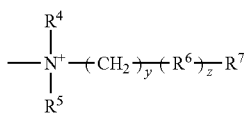
(Id)

$R^6$ is

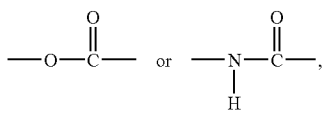

$R^7$ is a monovalent hydrocarbon radical having 1 to 22 carbon atoms,
y is 0 to 6
z is 0 or 1,
$A^-$ is an inorganic or organic anion which originates from a physiologically compatible acid HA,
S is H, or a polyalkylene oxide polyether of the general formula

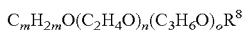

in which
m is 1 to 6,
n,o independently of one another are 0 to 100 and the polyether has a molecular weight between 100 and 6000 g/mol and
$R^8$ is H or an optionally branched aromatic or alicyclic hydrocarbon radical optionally containing double bonds and having 2 to 30 carbon atoms, or a UV-absorbing group,
$R^{11}$ is an aliphatic or aromatic hydrocarbon radicals having 1 to 30 carbon atoms which are optionally branched or H,
x is 0 or 1 and
a independently of the others has a value of from 4 to 1000, and
b has a value from 0 to 10.

2. The compound as claimed in claim 1, wherein at least one of the radicals $R^2$ carries a guanidino group, and $R^1$ is selected from the group consisting of be a methyl, ethyl, n-propyl, isopropyl, n-butyl, iso-butyl and phenyl radical.

3. The compound as claimed in claim 1, wherein M is identical or different and is one of the radicals selected from the group

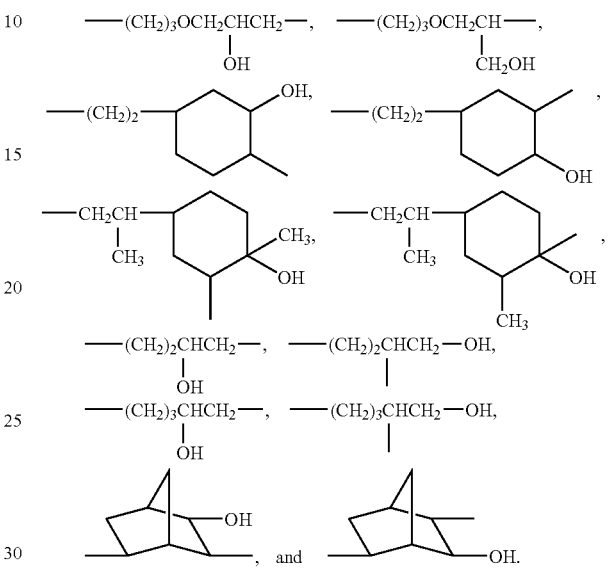

4. The compound as claimed in claim 1, wherein $A^-$, an inorganic or organic anion, originating from a physiologically compatible acid HA is selected from the group consisting of carbonic acid, phosphoric acid, hydrochloric acid, sulfuric acid, and formic acid, acetic acid, propionic acid, heptanoic acid, caprylic acid, nonanoic acid, capric acid, undecanoic acid, lauric acid, myristic acid, palmitic acid, stearic acid, arachidic acid, behenic acid, cyclopentanecarboxylic acid, cyclohexanecarboxylic acid, acrylic acid, methacrylic acid, vinylacetic acid, crotonic acid, 2-/3-/4-pentenoic acid, 2-/3-/4-/5-hexenoic acid, lauroleic acid, myristoleic acid, palmitoleic acid, oleic acid, gadoleic acid, sorbic acid, linoleic acid, linolenic acid, pivalic acid, ethoxyacetic acid, phenylacetic acid, lactic acid, 2-ethylhexanoic acid, oxalic acid, glycolic acid, malic acid, malonic acid, succinic acid, tartaric acid, glutaric acid, citric acid, adipic acid, pimelic acid, suberic acid, azelaic acid, sebacic acid, benzoic acid, o-/m-/p-toluic acid, phenylacetic acid, salicylic acid, 3-/4-hydroxybenzoic acid, p-toluenesulfonic acid, benzoic acid, salicylic acid, cinnamic acid, 4-methoxycinnamic acid, 4-aminobenzoic acid, 4-bis(hydroxypropyl)aminobenzoic acid, 4-bis(polyethoxy)aminobenzoic acid, 4-dimethylaminobenzoic acid, 3-imidazol-4-ylacrylic acid, 2-phenylbenzimidazole-5-sulfonic acid, 3,3'-(1,4-phenylenedimethine)bis (7,7-dimethyl-2-oxo-bicyclo[2.2.1]heptane-1-methansulfonic acid), 2-hydroxy-4-methoxybenzophenone-5-sulfonic acid, 3-(4'-sulfo)benzylidenebornan-2-one phthalic acid, completely or partially hydrogenated derivatives of the aforementioned acids, and mixtures thereof.

5. The compound as claimed in claim 1, wherein each Q is identical or different and is a cationic radical selected from the group consisting of capryldimethylamine, lauryldimethylamine, cocodimethylamine, myristyldimethylamine, cetyldimethylamine, stearyldimethylamine, behenyldimethylamine, oleyldimethylamine, capryloylamidopropyldimethylamine, lauramidopropyldimethylamine, cocamidopropyldimethylamine, myristamidopropyldimethylamine, palmitamidopropyldimethylamine, stearamidopropyldimethylamine, behenamidopropyldimethylamine, oleamidopropyldimethylamine, undecylenamidopropyldimethylamine, ricinoleamidopropyldimethylamine, and guanidinopropyldimethylamine.

6. A method of producing the polysiloxanes as claimed in claim 1, wherein M is a divalent or polyvalent hydrocarbon radical having at least 4 carbon atoms which has one hydroxyl group and which is interrupted by a nitrogen or quaternary ammonium group, wherein a siloxane containing at least one epoxy group is reacted at elevated temperature with guanidine compounds of the general formula

Z-G, in which
G which is as defined in claim 1 and
Z is a hydrocarbon radical containing at least 2 carbon atoms and nitrogen, which is optionally bonded to $R^{3'}$ via a carbon atom or heteroatom and in so doing forms a 5- to 8-membered ring,
and/or salts thereof.

7. The method of claim 6, wherein Z is a hydrocarbon radical containing 3-6 carbon atoms, and optionally comprising heteroatoms, which is optionally bonded to $R^{3'}$ via a carbon atom or heteroatom and in so doing forms a 5- to 8-membered ring.

8. A method of improving the mechanical structure of hair which comprises administering a hair treatment composition containing a compound as claimed in claim 1.

9. A method of improving the mechanical structure of hair which comprises administering a hair aftertreatment composition containing a compound as claimed in claim 1.

10. A hair treatment composition or hair aftertreatment composition comprising
    (a) 0.05 to 10% by weight of at least one of the compounds as claimed in claims 1,
    (b) 0 to 10% by weight of one or more emulsifiers,
    (c) 0 to 10% by weight of one or more consistency regulators,
    (d) 0 to 10% by weight of one or more cationic surfactants,
    (e) 0 to 20% by weight of one or more cosmetic oils or emollients,
    (f) a cosmetically acceptable auxiliary and/or additives,
    (g) one or more hair cosmetic active ingredients selected from the group consisting of protein hydrolysates of vegetable or animal origin based on keratin, collagen, elastin, wheat, rice, soya, milk, silk, corn or vitamins, panthenol, pyrrolidonecarboxylic acid, bisabolol, plant extracts, creatine, ceramides, and UV-absorbing agents.

11. A method of improving the shine on a surface which comprises administering a care formulation containing a compound as claimed in claim 1.

12. The polysiloxane of claim 1, wherein
$R^1$ is selected from the group consisting of a methyl, ethyl, n-propyl, isopropyl, n-butyl, iso-butyl and phenyl radical,
$R^3$ is independently, a hydrogen or an optionally branched hydrocarbon radical optionally comprising double bonds wherein the number of carbons in the hydrocarbon radical is from 1-4 carbon atoms, or
$R^{3'}$ is $R^3$ or an alkylene group which is joined to M via 3-4 carbon atoms and forms a 5- to 6-membered ring, and
$R^8$ is H or an optionally branched aromatic or alicyclic hydrocarbon radical optionally containing double bonds and having 4 to 22 carbon atoms, or a UV-absorbing group which is cinnamic acid or methoxycinnamic acid,
$R^{11}$ is an aliphatic or aromatic hydrocarbon radicals having 1 to 4 carbon atoms which are optionally branched or H,
a has a value of from 20 to 200
m is 3 to 6,
n,o is 0 to 20,
M is identical or different and is one of the radicals selected from the group

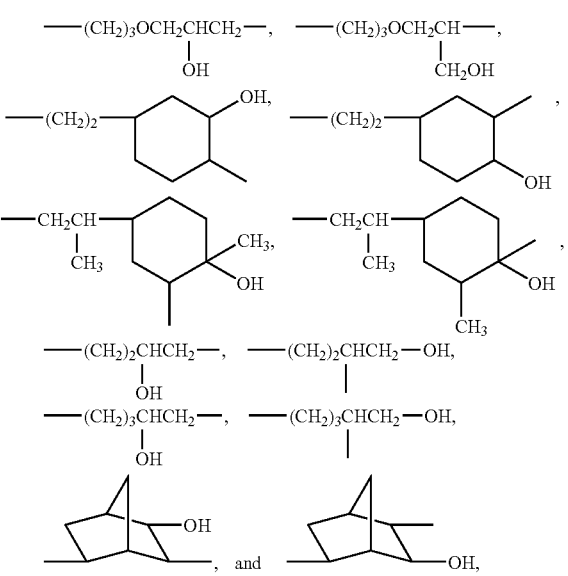

$A^-$ is an inorganic or organic anion, originating from a customary physiologically compatible acid HA selected from the group consisting of carbonic acid, phosphoric acid, hydrochloric acid, sulfuric acid, and formic acid, acetic acid, propionic acid, heptanoic acid, caprylic acid, nonanoic acid, capric acid, undecanoic acid, lauric acid, myristic acid, palmitic acid, stearic acid, arachidic acid, behenic acid, cyclopentanecarboxylic acid, cyclohexanecarboxylic acid, acrylic acid, methacrylic acid, vinylacetic acid, crotonic acid, 2-/3-/4-pentenoic acid, 2-/3-/4-/5-hexenoic acid, lauroleic acid, myristoleic acid, palmitoleic acid, oleic acid, gadoleic acid, sorbic acid, linoleic acid, linolenic acid, pivalic acid, ethoxyacetic acid, phenylacetic acid, lactic acid, 2-ethylhexanoic acid, oxalic acid, glycolic acid, malic acid, malonic acid, succinic acid, tartaric acid, glutaric acid, citric acid, adipic acid, pimelic acid, suberic acid, azelaic acid, sebacic acid, benzoic acid, o-/m-/p-toluic acid, phenylacetic acid, salicylic acid, 3-/4-hydroxybenzoic acid, p-toluenesulfonic acid, benzoic acid, salicylic acid, cinnamic acid, 4-methoxycinnamic acid, 4-aminobenzoic acid, 4-bis-(hydroxypropyl)aminobenzoic acid, 4-bis(polyethoxy)aminobenzoic acid, 4-dimethylaminobenzoic acid, 3-imidazol-4-ylacrylic acid, 2-phenylbenzimidazole-5-sulfonic acid, 3,3'-(1,4-phenylenedimethine)bis(7,7-dimethyl-2-oxo-bicyclo[2.2.1]heptane-1-methansulfonic acid), 2-hydroxy-4-methoxybenzophenone-5-sulfonic acid, 3-(4'-sulfo)benzylidenebornan-2-one phthalic acid, completely or partially hydrogenated derivatives of the aforementioned acids, and mixtures thereof; and Q is identical or different and is a cationic radical selected from the group consisting of capryldimethylamine, lauryldimethylamine, cocodimethylamine, myristyldimethylamine, cetyldimethylamine, stearyldimethylamine, behenyl dimethylamine, oleyldimethylamine, capryloylamidopropyldimethylamine, lauramidopropyldi methylamine, cocamidopropyldimethylamine, myristamidopropyldimethylamine, palmitami dopropyldimethylamine, stearamidopropyldimethylamine, behenamidopropyldimethylamine, oleamidopropyl dimethylamine, undecylenamidopropyldimethylamine, ricinoleamidopropyl dimethylamine, and guanidinopropyldimethylamine.

13. A method of providing a drying auxiliary to a car wash composition which comprises of adding a compound of claim 1 to the car wash composition.

* * * * *